United States Patent [19]

Lukasavage et al.

[11] Patent Number: 5,124,493
[45] Date of Patent: Jun. 23, 1992

[54] IMPROVED PROCESS OF PRODUCING HMX IN 100% YIELD AND PURITY

[75] Inventors: William Lukasavage, Succasunna; Steven Nicolich, Saddlebrook; Jack Alster, Fair Lawn, all of N.J.

[73] Assignee: The United States of America as represented by the Secretary of the Army, Washington, D.C.

[21] Appl. No.: 775,402

[22] Filed: Oct. 15, 1991

[51] Int. Cl.$^5$ .......................................... C07D 257/06
[52] U.S. Cl. ..................................... 568/924; 149/92; 149/105; 149/106; 540/475
[58] Field of Search .................. 568/924; 149/92, 105, 149/106; 540/475

[56] References Cited

U.S. PATENT DOCUMENTS

| | | | |
|---|---|---|---|
| 3,415,868 | 12/1968 | Smetana et al. | 568/924 |
| 3,939,148 | 2/1976 | Siele et al. | 540/475 X |
| 4,432,902 | 2/1984 | McGuire et al. | 540/475 |
| 4,534,895 | 8/1985 | Frankel et al. | 540/475 |
| 4,614,800 | 9/1986 | Willer et al. | 540/475 X |
| 4,920,859 | 4/1989 | Millar et al. | 558/483 |

Primary Examiner—John S. Maples
Assistant Examiner—C. Sayala
Attorney, Agent, or Firm—Anthony T. Lane; Edward Goldberg; Edward F. Costigan

[57] ABSTRACT

An improvement when 1,3,5,7-tetranitro-1,3,5,7-tetraazacyclooctane is prepared by nitrolysis of 1,3,5,7-tetraacyl-1,3,5,7-tetraazaceyloctane with a solution of nitric acid and nitrogen pentoxide or phosphorous pentoxide. This improved process herein before set forth produces 99% yield and purity of product.

5 Claims, No Drawings

IMPROVED PROCESS OF PRODUCING HMX IN 100% YIELD AND PURITY

GOVERNMENTAL INTEREST

The Government has rights in this invention pursuant to Contract No. DAAA86-C-0171 awarded by Department of the Army.

The invention described herein was made in the course of or under a contract or subcontract thereunder with the Government and may be manufactured, used and licensed by or for the Government for Governmental purposes without the payment to us of any royalties thereon.

FIELD OF USE

This invention relates to an improved process of making HMX.

BACKGROUND OF THE INVENTION

HMX, which is known as (1,3,5,7-tetranitro-1,3,5,7-tetraazacyclooctane), is the most powerful non-atomic explosive in military use, but widespread use of this explosive has been limited by its exceptionally high cost. Although HMX was first discovered in 1941, the only known process for its manufacture comprises nitrolysis of hexamethylenetetramine with a mixture of nitric acid and acetic anhydride, essentially as described by Castorina and co-workers (J.A.C.S., 82, 1617 (1960). The latter process has many deficiencies, notably there is a very poor yield of HMX on a methylene basis, and a very high consumption of acetic anhydride required during processing.

It has been proposed to produce HMX by nitrolysis of TAT, which is known as 1,3,5,7-tetraacetyl-1,3,5,7-tetraazacyclooctane. However, such attempts at this nitration have proved to be largely and very frequently unsuccessful.

These attempts have included treatment of TAT with the following, viz. (a) treatment with 100% nitric acid at temperatures ranging from $-30°$ C. to $50°$ C.; (b) treatment with mixtures of ammonium nitrate and acetic anhydride at $70°$ C.; and (c) treatment with mixtures of 100% nitric acid and acetic anhydride at temperatures from $0°$ to $25°$ C. Further techniques were used which included heavy treatment with dinitrogen pentoxide which is very expensive, or the use of phosphorous pentoxide, which is somewhat troublesome to use.

The products of the first two procedures cited above were not water-insoluble, while the third procedure produced a water insoluble product which was not even HMX. The last process utilized yielded HMX of good quality and a very slightly higher yield than the process of the art, but the reaction requires the use of elevated temperatures and very, very high amounts of very expensive reagents, such as nitrogen pentoxide and the like.

SUMMARY OF THE INVENTION

An object of the present invention is to provide a cost effective process for producing HMX in essentially a yield of 95 to 100% by nitrolysis of TAT. In other words, it cost less to produce the HMX, which makes the process commercially attractive. Other objects will become apparent from the following description of the invention.

We have discovered that by the use of the process of this invention, HMX can be obtained in quantitative yield, and at $99+\%$ purity, by reacting TAT with $98+\%$ nitric acid, for more prolonged periods at lower and acceptable temperatures viz. $20°$ to $45°$ C. The new milder conditions require less than three mole equivalents of dinitrogen pentoxide or phosphorous pentoxide per mole of TAT. This is substantially quite less than the simple stoichiometric requirement, and about a 90% reduction over that employed in the prior art, U.S. Pat. No. 3,939,148.

Other outstanding features, which are unique to this process are that the yield of the product is essentially 100%, and that the purity of the product is essentially 100%. Due to the fact that the product is 100% pure, there are no recrystallization processes necessary. Also, there are not any by-products produced during the reaction process, including no RDX contamination, at all, so that there are not any resulting environmental problems. This is an essentially isothermal room temperature process having no requirement for heating or cooling, and therefore no utility costs at all. Since the process produces no heat at all, overheating is not a problem. Further, with some apparent designs, even stirring is not required. There are no excess reagents consumed, so therefore, no costly recycles of any reagents are required or necessary. And, very importantly, for explosive production, the reaction may be performed with much greatly enhanced safety by operating at temperatures as low as room temperature.

We have found no excessive amount of any reagent necessary, or desirable to the process of this invention. Further, the mild temperatures, typically employed during this synthesis or process, do not create an unduly hostile environment for this product. The nitrogen pentoxide may be introduced, as such in the reaction mixture, or it may be generated in situ as is known in the art. This is generally accomplished by employing a mixture of nitric acid with a substance which is capable of reacting with nitric acid, under the conditions employed, to produce nitrogen pentoxide.

The process of the present invention is considered to be novel because prior art attempts to produce HMX by nitrolysis of TAT has been largely and repeatedly unsuccessful. Even when 100% nitric acid was mixed with acetic anhydride, the process was very unsuccessful in the amount of yield produced of the product. Also, prior attempts to make HMX with nitrogen pentoxide and phosphorous pentoxide clearly required a much greater amount of each and every one of the reagents. And, it is to be noted, that even when more than ten times as much phosphorous pentoxide was employed in the art, a 79% yield was never exceeded.

DESCRIPTION OF THE PREFERRED EMBODIMENTS

The following examples illustrate specific embodiments of the method of carrying out the process of the present invention. It is to be understood that they are illustrative only and do not in any way limit the invention.

EXAMPLE 1

Nitration of TAT with a Mixture of Nitric Acid and Phosphorous Pentoxide 500 grams of 98% nitric acid were introduced into a 1000 ml. beaker, provided with a thermometer, and a magnetic stirring bar. Then, 70 grams of phosphorous pentoxide were added in very controlled portions, based on temperatures, over a 30 minute period. The addition was made with stirring, via the magnetic stirring bar, and the rate of addition of the phosphorous pentoxide was, as stated, dictated by the temperature of the reaction mixture. Note, the latter temperature was not permitted to rise above 35 degrees Centigrade. The reaction mixture was allowed to stir covered by a piece of aluminum foil until the temperature fell to room temperature. At this point, 50 grams of TAT were than added, in about 4 equal portions, but at such a rate that the temperature was prevented from rising above 40 degrees Centigrade. This is very important. The reaction mixture was then allowed to fall to room temperature, and the stirring stopped. The stirring bar was removed, when all signs of any exothermic action had subsided. The beaker covered by aluminum foil was allowed to set undisturbed for 16 hours at room temperature. During this time, the entire reaction mixture sets-up to a cream cheese like consistency. The semi-solid was then spooned out of the beaker into 500 grams of very rapidly stirred water which was at room temperature. After thorough mixing, the HMX water solution was filtered and washed with hot water. This was done until the PH of the filtrate was the same as the wash water. The wet cake of crude HMX was than dispersed in 400 grams of boiling water, and filtered. This process was then repeated, if the melting point of the product was found to be less than 282 degrees Centigrade (99+purity). This purity was also confirmed by HPLC. No further treatment was required, either by repeated crystallizations, or by treatment with solvents, and the like to meet government specifications of purity. The typical yield of pure HMX ranges between 98 and 100%, but this depended primarily upon the initial purity of the TAT.

EXAMPLE 2

The same proportions and methods were employed as set forth in Example 1, however the temperature was held constant at 35 degrees Centigrade. Under these conditions, the reaction time was reduced to approximately 10 hours. The yield of product dropped slightly, ranging from 94 to 98%, with the purity maintained at 99+%.

EXAMPLE 3

The same proportions and methods were again employed as in Example 1. However, the temperature was held constant at 45 degrees Centigrade. Under these conditions, the reaction time was reduced to approximately 5 hours, with the yield ranging downward to 75 to 85%, while the purity remained constant to 99+%.

EXAMPLE 4

The same methods and temperature were used as set forth in Example 1,2, and 3, however, the quantity of nitric acid was increased to 600 grams. At this concentration, the reaction mixture remained a clear non viscous solution, and the mixture could be readily stirred. The reaction kinetics of the process are however reduced by dilution, and the reaction time is increased. At room temperature, the reaction time is increased from 16 hours to 48 hours.

EXAMPLE 5

The same methods and temperature were used as set forth in Example 1, 2, 3 , however, the phosphorous pentoxide is replaced by nitrogen pentoxide in the same molar quantity. The reaction proceeded much the same way, but the yields were between 10 to 20% lower than usual, but this depended upon the concentration of reactants and the temperature of the reaction.

EXAMPLE 6

Continuous Nitration of TAT with a Mixture of Nitric Acid and Phosphorous Pentoxide The procedure and proportions of Example 1, 2, 3 were used in this experiment, however, after 16 hours under conditions at room temperature, ½ of the reaction mixture was removed and worked-up as in Example 1. The removed portion is worked-up by the methods and with the proportions as outlined in Example 1. To the remaining reaction mass, a mixture made up of phosphorous pentoxide and TAT was added. The phosphorous pentoxide was added first, and at ½ the normal proportion to TAT being added. No additional nitric acid was added at this time. At this increased concentration, the reaction kinetics were greatly accelerated taking only about ¼ the normal 16 hours. The reduced amount of nitric acid used in this procedure means that less phosphorous pentoxide is required to remove traces of water from the nitric acid, so less of the latter material is required. Due to the presence of a mixture of TAT, HMX, and other by-product in the mixture, the more concentrated reaction mixture remained a clear and stirable solution. Once these operational conditions have been met, samples may be continuously removed and fresh make-up of nitric acid/phosphorous pentoxide and TAT were added in the proper proportions to maintain the reaction mixture at a constant size and concentration.

CONCLUSION

This invention makes it possible to prepare HMX in a highly quantitative and very pure form. The process of the present invention required very little energy. There were no excesses required in the amount of chemicals used during the various stages of the process. The present process is totally less expensive, totally environmentally acceptable, and most important, the process is inherently safer. All these advantages are achieved because the process operates at room temperature.

The Bachmann process is the only process which is commercially used. It is very inefficient, and has had many problems for the last 50 years. This process of the prior art has a maximum yield of only 64%. The remaining starting material ends up as hazardous waste. Further, this process of the art costs at least about 5 times that of the cost of the process of the present invention. Our process requires fewer steps, and very little energy consumption.

The process of the present invention almost doubles the yield of HMX, while requiring only half the materials required during processing. As a result, there is very little, if any, environmental impact. The meager use of energy and reactants reduces production cost by about 75%. The reaction is run at room temperature providing a greater safety margin. Also, the reaction does not produce any heat, so no costly cooling apparatus, chemicals or the like are required.

To summarize, the process of the present invention produces the highest yield and the highest purity of yield of any existing process. This is done in such a fashion that the least amount of energy consumption is necessary, and the least amount of by-products are produced compared to any existing process of the prior art. Further, no recrystallization is necessary to meet any and all government standards of purity.

The foregoing disclosure is merely illustrative of the principles of this invention and are not interpreted in a limiting sense. We wish it to be understood that we do not desire to be limited to the exact details described for obvious modifications will occur to a person skilled in the art.

What is claimed is:

1. In an improved process of making (1,3,5,7-tetranitro-1,3,5,7-tetraazacyclooctane) by the nitrolysis of 1,3,5,7-tetraacetyl-1,3,5,7-tetraazacyclooctane (TAT) with nitric acid and dinitrogen pentoxide or phosphorous pentoxide, the improvement consisting essentially of using between 5 to 10 g nitric acid per gram TAT, at a temperature between about 20° C. and about 45° C. for a time period between about 4 Hr. and about 16 Hr. to produce a quantitative yield of about 99% and a purity of 99% or more.

2. The process of claim 1 wherein the temperature is about 20° C. and the reaction time is about 16 Hr.

3. The process of claim 1 wherein the temperature is about 35° C. and the reaction time is about 10 Hr.

4. The process of claim 1 wherein the temperature is about 45° C. and the reaction time is about 5 Hr.

5. The process of claim 1 wherein the total amount of phosphorous pentoxide is less than 3 mole equivalents per mole of TAT.

* * * * *